United States Patent [19]

Arena

[11] Patent Number: 4,839,233
[45] Date of Patent: Jun. 13, 1989

[54] MEDICAL GRADE FILM AND METHOD OF STERILIZING THE SAME AND STERILIZED MEDICAL GRADE FILM

[75] Inventor: Arthur A. Arena, Trenton, N.J.
[73] Assignee: Huls America, Inc., Edison, N.J.
[21] Appl. No.: 37,043
[22] Filed: Apr. 10, 1987
[51] Int. Cl.$^4$ .................... B32B 27/22; B32B 27/20; C08K 5/15; C08K 3/30
[52] U.S. Cl. .................... 428/220; 523/105; 523/113; 524/114; 524/314; 524/423
[58] Field of Search ............. 523/103, 105, 113; 524/436, 394, 284, 178, 314, 114, 423; 428/220

[56] References Cited

U.S. PATENT DOCUMENTS

| | | | |
|---|---|---|---|
| 3,356,625 | 12/1967 | Giessler | 524/423 |
| 3,627,707 | 12/1971 | Giessler et al. | 524/423 |
| 3,824,202 | 7/1974 | White et al. | 524/305 |
| 3,940,325 | 2/1976 | Hirao | 260/23 XA |
| 4,026,852 | 5/1977 | White et al. | 260/23 XA |
| 4,057,672 | 11/1977 | Greekmore et al. | 428/220 |
| 4,278,718 | 7/1981 | Billings et al. | 524/296 |
| 4,329,182 | 5/1982 | Sugahara et al. | 106/243 |
| 4,412,897 | 11/1983 | Kornbaum et al. | 204/159.2 |
| 4,454,294 | 6/1984 | Zentner et al. | 526/344.3 |
| 4,515,666 | 5/1985 | Rekers | 204/159.2 |
| 4,515,916 | 5/1985 | Molt | 524/99 |
| 4,540,416 | 9/1985 | Hattori et al. | 525/240 |
| 4,551,497 | 11/1985 | Shinozuka et al. | 524/423 |
| 4,657,542 | 4/1987 | Ohachi | 523/105 |

*Primary Examiner*—Lewis J. Jacobs
*Attorney, Agent, or Firm*—Antonelli, Terry & Wands

[57] ABSTRACT

A medical grade film, a method of sterilizing a medical grade film and the sterilized medical grade film produced thereby, wherein the film contains a vinyl chloride resin, such as PVC, and barium sulfate. The film can be sterilized by exposure to gamma radiation of one to five megarads without any color change. Electron beam radiation may also be employed.

18 Claims, No Drawings

MEDICAL GRADE FILM AND METHOD OF STERILIZING THE SAME AND STERILIZED MEDICAL GRADE FILM

BACKGROUND OF THE INVENTION

This invention pertains to medical grade film and a method of sterilizing medical grade film and, more particularly, to medical grade film and a method of sterilizing the same wherein the film can be gamma or electron beam sterilized without any color change, and the sterilized medical grade film produced thereby.

Medical grade film, e.g., film meeting the requirements of Class VI plastics as set forth in the U.S. Pharmacopeia, Volume XX, is useful for manufacturing products which can be used for medical treatments and for manufacturing containers for products such as pharmaceuticals, cosmetics and foods. Suitable applications for such films are enteric feeding bags, kidney dialysis bags, barium enema bags, colostomy bags, bloodwashing bags, blood storage bags, urinary drainage bags, incontinent products, inflatable splints, hospital I.D. bracelets, traction devices, burn mattresses, comfort cushions and waterproof hospital sheeting.

Currently, the medical industry utilizes a medical grade film containing polyvinyl chloride (PVC) resin. The industry sterilizes this medical grade film using ethylene oxide. However, this is a cumbersome, time-consuming and expensive method of sterilization. The industry prefers using the gamma-radiation sterilization method since it is more effective biologically, less expensive and less time-consuming. However, irradiation levels of 1 to 5 megarads used in this sterilization method cause the polyvinyl film to yellow. While this yellowing does not render the film nonfunctional, it is considered undesirable aesthetically.

SUMMARY OF THE INVENTION

Accordingly, it is an object of the present invention to provide a medical grade film which may be gamma or electron beam sterilized without any color change.

It is a further object of the present invention to provide a method of sterilizing a medical grade film with gamma or electron beam radiation without any color change in the film.

It is an additional object of the present invention to provide a sterilized medical grade film.

These objects are accomplished by providing a halogen containing resin film including barium sulfate. The halogen containing resin is preferably a vinyl chloride resin such as PVC. In addition to polyvinyl chloride and varium sulfate, the film can also contain a plasticizer such as di-2-ethylhexyl adipate, epoxidized soybean oil, a stabilizer such as an organo zinc soap blend or an organotin salt, and a lubricant such as stearic acid.

The medical grade film of the present invention can be successfully gamma or electron beam sterilized without any color change. For example, gamma radiation doses can range from 1 to 5 megarads.

DESCRIPTION OF THE PREFERRED EMBODIMENTS

A medical grade film of the present invention includes a halogen containing resin and, more particularly, a vinyl chloride resin. The vinyl chloride resin may be a homopolymer of vinyl chloride or a mixed polymer, such as copolymers or graft polymers of vinyl chloride which have been prepared by known continuous or batch polymerization processes. Suitable monomers for copolymerization with vinyl chloride are olefins, vinyl esters of carboxylic acids, acrylonitrile, styrene and cyclohexylmaleimide. Polymers useful for graft polymerization with vinyl chloride include elastomeric polymers of butadiene, ethylene, propylene, styrene and/or acrylonitrile.

The medical grade film of the present invention may contain any of a number of known stabilizers. Suitable stabilizers include organo zinc soap blends and metallic soaps of calcium and zinc. A preferable stabilizer is Mark QTS (an organo zinc soap blend manufactured by Argus Chemical Division of Witco Chemical Corp.).

The medical grade film of the present invention may contain any of a number of known lubricants. Such lubricants include calcium stearate, hydrogenated tallow and fatty acids (food grade). Preferably lubricants include stearic acid and calcium stearate.

Known plasticizers may also be included in the medical grade film of the present invention. Examples of such plasticizers are phthalate plasticizers such as dioctyl phthalate (D.O.P.). However, the preferred plasticizer is di-2-ethylhexyl adipate.

The medical grade film may contain other additives such as epoxidized soybean oil and FDA approved pigments.

The advantageous effects of the present invention are obtained by including barium sulfate in the medical grade film.

The foregoing raw materials are preferably included in the medical grade film of the present invention in the following proportions by weight percent: the amount of PVC resin preferably contained in the composition is 60 to 69%; the amount of plasticizer is preferably 19 to 25%; the amount of stabilizer is preferably 0.5 to 1.3%; the amount of lubricant is preferably 0.15 to 0.2%; the amount of epoxidized soybean oil is preferably 9.5 to 10.5%; and the amount of barium sulfate is preferably 0.5 to 5%, most preferably 2.9%.

The raw materials can be mixed by blending then Banburying. The composition obtained thereby can then be calendered to form films having a thickness in the range of 2 to 30 mils, preferably 6 to 18 mils.

The films can be shaped by known techniques such as electronic heat sealing to form useful articles.

Sterilization is preferably accomplished by exposing the films or shaped articles to gamma radiation. Gamma radiation sources are known in the art, e.g., a cobalt 60 source may be used. Typical irradiation levels are in the range of 1 to 5 megarads. Electron beam radiation may also be employed.

EXAMPLE 1

A film was prepared by blending the following raw materials followed by Banburying and calendering:

PVC resin—100 parts by weight,

Di-2-ethylhexyl adipate (DOA plasticizer)—33 parts by weight,

Mark QTS (manufactured by Argus Chemical Division of Witco Chemical Corp.)—0.75 parts by weight, Drapex 6.8 (epoxidized soybean oil manufactured by Argus Chemical Division of Witco Chemical Corp.)—15 parts by weight, Barium sulfate—4.47 parts by weight, and Industrene 7018 FG (Food Grade 70% stearic acid manufactured by Humko Chemical Division of Witco Chemical Corp.)—0.25 parts by weight.

The film was successfully sterilized using 1 to 5 megarads of gamma radiation without any color change.

Large scale processing of the film can be accomplished in the following manner. The PVC resin can be stored in resin silos. Bulk plasticizer such as D.O.P. and epoxidized soybean oil can be stored in separate plasticizer tanks. Bulk PVC resin, D.O.P. and epoxidized soybean oil can be pumped and weighed into blenders. The other ingredients, such as lubricants and barium sulfate, can be kept in drums and/or bags and can be weighted into the blender. The total weight of the raw materials in the blender can be approximately 4,000 lbs. These materials are then blended for 25 minutes at approximately 200° F.

Two-hundred-fifty pounds of the blended raw materials are then transferred into the Banbury where the materials are mixed for 3½ minutes, reaching a temperature of 340° F., until the formulation is fused. The plastic formulation is then transferred to a two-roll mill which is at a temperature of 320° F. This mill performs the function of mixing and storage.

The material is then transferred to an extruder-strainer which is at a temperature of 325° F. The material is strained and extruded into a continuous web approximately 3 inches in diameter which is fed to a calender. A calender, such as a four-roll inverted-L calender, can be used. The calender rolls are heated, top to bottom, from 350° F. to 310° F. The calender forms the (webbed) material into a sheet of various widths and thickness. The calender sheet is then cooled by cooling drums and a beta gauge measures the thickness of the sheet. A winder rolls the sheet into a roll which is then slit into smaller rolls on a slitter. The rolls can then be packaged into, e.g., a polyethylene bag which is wrapped with Kraft paper. The thus-formed medical grade film can be used to fabricate desired products by conventional electronic heat sealing equipment. The film or products can be sterilized using gamma or electron beam radiation.

While the invention has been described and illustrated by the example included herein, it is not intended that the invention be strictly limited thereto, and other variations and modifications may be employed within the scope of the following claims.

What is claimed is:

1. A radiation sterilized medical grade film which does not exhibit any color change upon sterilization by gamma radiation, comprising a vinyl chloride resin and barium sulfate, wherein said medical grade film has been sterilized by irradiation with 1 to 5 megarads of gamma radiation.

2. A radiation sterilized medical grade film according to claim 1, wherein said vinyl chloride resin is polyvinyl chloride.

3. A radiation sterilized medical grade film according to claim 2, further comprising a plasticizer.

4. A radiation sterilized medical grade film according to claim 3, further comprising a stabilizer, a lubricant and epoxidized soybean oil.

5. A radiation sterilized medical grade film according to claim 3, wherein said plasticizer is di-2-ethylhexyl adipate.

6. A radiation sterilized medical grade film according to claim 1, wherein said medical grade film consists essentially of polyvinyl chloride, di-2-ethylhexyl adipate, an organotin salt, epoxidized soybean oil, stearic acid and barium sulfate.

7. A radiation sterilized medical grade film which does not exhibit any color change upon sterilization by gamma radiation, comprising a vinyl chloride resin and barium sulfate, wherein said film has a thickness in the range of 2-30 mils.

8. A radiation sterilized medical grade film according to claim 7, wherein said film has a thickness in the range of 6-18 mils.

9. A radiation sterilized medical grade film which does not exhibit any color change upon sterilization by gamma radiation, comprising a vinyl chloride resin, barium sulfate and a plasticizer, wherein said vinyl chloride resin is polyvinyl chloride, and wherein said film has a thickness in the range of 2-30 mils.

10. A radiation sterilized medical grade film according to claim 9, wherein said film has a thickness in the range of 6-18 mils.

11. A radiation sterilized medical grade film which does not exhibit any color change upon sterilization by gamma radiation and which consists essentially of 60-69 wt. % polyvinyl chloride, 19-25 wt. % plasticizer, 0.5-1.3 wt. % stabilizer, 0.15-0.2 wt. % lubricant, 9.5-10.5 wt. % epoxidized soybean oil, and 0.5-5 wt. % barium sulfate.

12. A radiation sterilized medical grade film according to claim 11, wherein the amount of said barium sulfate is 2.9 wt. %.

13. A radiation sterilizable medical grade film comprising a vinyl chloride resin, barium sulfate and a plasticizer, wherein said film is capable of being sterilized by high energy radiation without exhibiting a change in color, and wherein said film is capable of being sterilized by 1 to 5 megarads of gamma radiation without exhibiting a change in color.

14. A radiation sterilizable medical grade film according to claim 13, further comprising a stabilizer, a lubricant and epoxidized soybean oil.

15. A radiation sterilizable medical grade film according to claim 13, wherein said plasticizer is di-2-ethylhexyl adipate and said vinyl chloride resin is polyvinyl chloride.

16. A radiation sterilizable medical grade film which is capable of being sterilized by high energy radiation without exhibitng a change in color, and which consists essentially of 60-69 wt. % polyvinyl chloride, 19-25 wt. % plasticizer, 0.5-1.3 wt. % stabilizer, 0.15-0.2 wt. % lubricant, 9.5-10.5 wt. % epoxidized soybean oil, and 0.5-5 wt. % barium sulfate.

17. A radiation sterilized medical grade film according to claim 1, wherein said medical grade film consists essentially of polyvinyl chloride, di-2-ethylhexyl adipate, an organo zinc soap blend, epoxidized soybean oil, stearic acid and barium sulfate.

18. A radiation sterilized medical grade film according to claim 1, wherein said medical grade film consists essentially of polyvinyl chloride, di-2-ethylhexyl adipate, a metallic soap of calcium and zinc, epoxidized soybean oil, stearic acid and barium sulfate.

* * * * *